United States Patent [19]

DeMarinis

[11] 4,320,148

[45] Mar. 16, 1982

[54] 2-AMINOTETRALIN COMPOUNDS, PHARMACEUTICAL COMPOSITIONS AND METHOD OF PRODUCING CENTRAL ALPHA$_1$ AGONIST ACTIVITY

[75] Inventor: Robert M. DeMarinis, Ardmore, Pa.

[73] Assignee: SmithKline Corporation, Philadelphia, Pa.

[21] Appl. No.: 210,470

[22] Filed: Nov. 24, 1980

[51] Int. Cl.$^3$ .................... A01N 33/02; C07C 87/64; A61K 31/135
[52] U.S. Cl. .............................. 424/330; 260/501.18; 260/501.19; 424/316; 564/219; 564/220; 564/222; 564/414; 564/428
[58] Field of Search ................ 564/428; 424/316, 330; 260/501.18

[56] References Cited

U.S. PATENT DOCUMENTS

| | | | |
|---|---|---|---|
| 3,253,037 | 5/1966 | Huebner | 564/428 |
| 3,637,740 | 1/1972 | Sarges | 564/428 X |
| 4,096,173 | 6/1978 | Molloy | 564/428 X |

OTHER PUBLICATIONS

Aminotetralin Analogs of Methoxamine as Potential Hypertensive Agents, Sharabi et al., *Research Communications in Chemical Pathology and Pharmacology*, vol. 19, No. 1, Jan. 1978, pp. 37–53.

*Primary Examiner*—Robert V. Hines
*Attorney, Agent, or Firm*—Joseph A. Marlino; Alan D. Lourie; Richard D. Foggio

[57] ABSTRACT

2-Aminotetralin compounds having 5- and 8- substituents are centrally acting alpha$_1$ agonists.

16 Claims, No Drawings

2-AMINOTETRALIN COMPOUNDS, PHARMACEUTICAL COMPOSITIONS AND METHOD OF PRODUCING CENTRAL ALPHA₁ AGONIST ACTIVITY

This invention relates to new 2-aminotetralin compounds having 5- and 8- substituents. These compounds have pharmacological activity, in particular they are alpha₁ agonists.

The catecholamine theory of depression is that the depression is caused by lack of norepinephrine in the synaptic cleft of central noradrenergic nerve endings resulting in inadequate activation of the postsynaptic alpha₁ receptor.

The compounds of this invention are capable of producing direct stimulation of central postjunctional alpha₁ receptors by mimicking the action of norepinephrine and restoring the normal postsynaptic activity. They are therefore direct acting alpha₁ agonists which are associated with antidepressant activity.

The compounds of this invention, and which are the active ingredients of the pharmaceutical compositions and methods of this invention, are represented by the following formula:

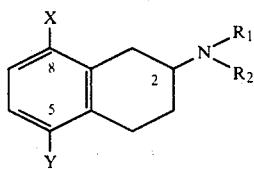

Formula 1 in which:

R₁ and R₂ are hydrogen or lower alkyl having not in excess of three carbon atoms;

X is methoxy and Y is methylthio, ethylthio, phenylthio, trifluoromethylthio or amino; or Y is methoxy and X is methylthio, ethylthio, phenylthio, trifluoromethylthio or amino;

and pharmaceutically acceptable, acid addition salts thereof.

The compounds of this invention are prepared by the following procedure:

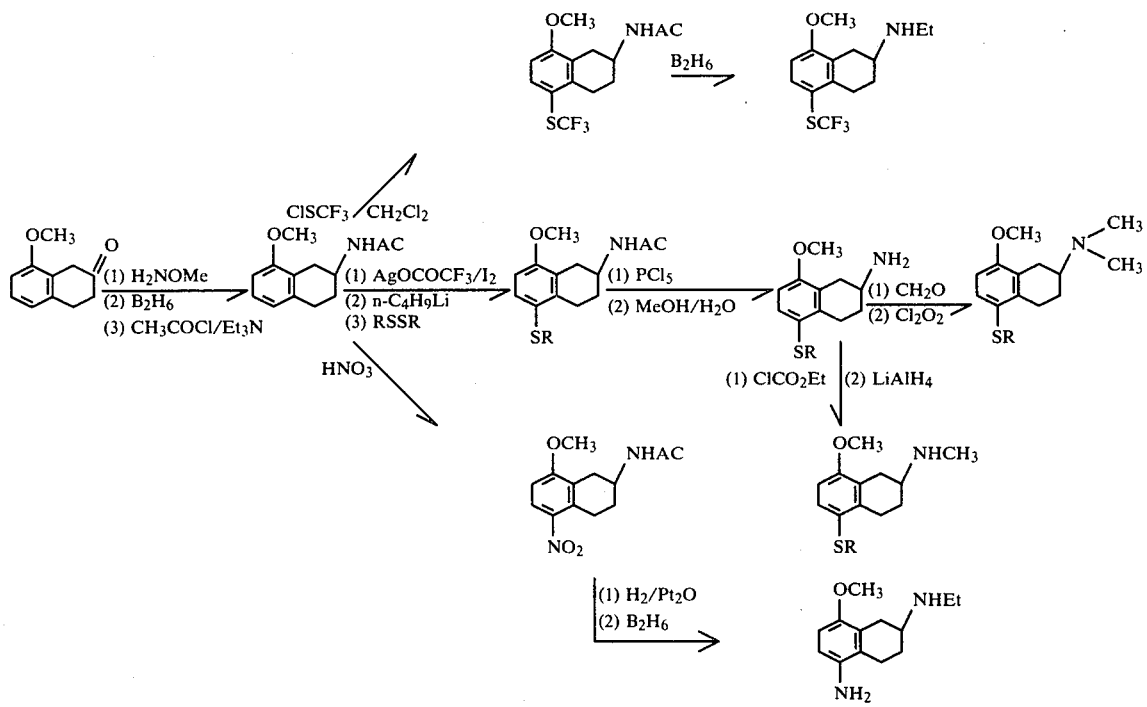

R = lower alkyl of 1-3 carbons

According to the above procedure, 8-methoxy-2-tetralone is converted to the corresponding acetamide by forming the O-methyl oxime, reducing the oxime to the amine and acetylating the amine to the acetamide. Electrophilic substitution at the 5-position of the acetamide is then carried out with the desired substituents as disclosed above. For example, when the amino substituent is required, the acetamide is treated with nitric acid and then reduced with any well known reducing agent, hydrogen in the presence of platinum oxide being an advantageous reducing agent. When the phenylthio or alkylthio substituent is desired, the acetamide is treated with silver trifluoromethyl acetate and iodine. The iodine is displaced in a further reaction with n-butyl lithium and the appropriate disulfide. The trifluoromethylthio derivative is obtained by treating the 8-methoxyacetamide derivative with trifluoromethyl sulfenyl chloride. Reduction or hydrolysis of the acetamide group results in the corresponding amino or ethyl substituted amino derivative. The 2-(N-methyl) derivative is obtained by the reaction of the corresponding 2-amino compound with ethyl chloroformate followed by reduction with lithium aluminum hydride. The N,N-dimethyl derivative is prepared by reacting the corresponding 2-amino compound with formic acid and formaldehyde.

When the 5-methoxy-8-substituted-2-aminotetralin compounds are desired, 5-methoxy-2-tetralone is substituted as a starting material for the 8-methoxy-2-tetralone followed by the above disclosed procedures.

Pharmaceutically acceptable acid addition salts of the compounds of Formula 1 are formed with organic and inorganic acids by methods known to the art. The base is treated with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

The basic activity of the compounds of this invention is demonstrated in vitro by determining the selective postjunctional alpha$_1$ adrenergic agonist activity using the isolated rabbit aortic strip. The assay procedure is described by Steinsland et al. *J. Pharm. Exp. Ther.* 184:346–356, 1973. Briefly, this test comprises sacrificing a white rabbit and removing the central ear artery. The artery is cannulated at both ends and placed in a perfusion chamber. The artery is simultaneously perfused intraluminally and superfused extraluminally with Krebs solution. The compound to be tested can be administered by means of either the intraluminal or extraluminal flow. The sympathetic nerve is excited at four minute intervals by field stimulation. The selective alpha$_1$ agonist activity is measured as the ability to increase perfusion pressure (mm Hg.) without inhibiting response to sympathetic nerve stimulation.

A quantitation of postjunctional alpha$_1$ agonist activity (EC$_{50}$) is determined for compounds showing activity in the above test. This is accomplished by employing an isolated segment of rabbit ear artery. The segment is mounted in a chamber superfused with oxygenated Krebs solution. The segment is suspended between two tungsten wires, one attached to the chamber, the other to a force-displacement transducer so that smooth muscle tension can be measured directly. Before administration of the test drug, norepinephrine is administered in increasing concentration ($10^{-8}$ M to $3 \times 10^{-6}$ M) to determine maximum response of the artery. The dose required to produce 50% of the maximum response is the EC$_{50}$.

2-Aminotetralin compounds having 5,8-dimethoxy substituents are generally known in the art. These compounds are disclosed in *Res. Commun. Chem. Path. Pharmacol.* 19:37–53, 1978 as peripheral hypertensive agents.

The EC$_{50}$ of preferred compounds of this invention, 1,2,3,4-tetrahydro-8-methoxy-N,N-dimethyl-5-(methylthio)-2-naphthalenamine and 1,2,3,4-tetrahydro-8-methoxy-5-(methylthio)-2-naphthalenamine, were compared to the known 5,8-dimethoxy compounds. Following are the results:

TABLE I

Structure

| SK&F Number | X | R$_1$ | R$_2$ | EC$_{50}$ |
|---|---|---|---|---|
| 89,900 | SCH$_3$ | CH$_3$ | CH$_3$ | $1.3 \times 10^{-8}$ |
| 89,748 | SCH$_3$ | H | H | $9.3 \times 10^{-9}$ |
| 88,444 | OCH$_3$ | CH$_3$ | CH$_3$ | $1.0 \times 10^{-7}$ |
| 87,696 | OCH$_3$ | H | H | $1.1 \times 10^{-7}$ |

The results clearly demonstrate that when a methylthio group is substituted for the methoxy group of the known compound, the alpha$_1$ agonist activity is enhanced at least tenfold.

The pharmaceutical compositions of this invention having alpha$_1$ agonist activity comprise a pharmaceutical carrier and, as the active ingredient, a 2-aminotetralin compound of Formula 1. The active ingredient will be present in the compositions of this invention in an effective amount to produce alpha$_1$ agonist activity.

Preferably, the compositions of this invention contain the active ingredient of Formula 1 in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of producing alpha$_1$ agonist activity according to this invention comprises administering to an animal in an amount sufficient to produce alpha$_1$ agonist activity a 2-aminotetralin compound of Formula 1.

Preferably, the compounds of Formula 1 are administered in conventional dosage unit forms prepared by combining an appropriate dose of the compound with standard pharmaceutical carriers.

Preferably, the active ingredient of Formula 1 will be administered in a daily dosage regimen of from about 100 mg. to about 2000 mg., most preferably from about 200 mg. to about 1000 mg. Advantageously, equal doses will be administered preferably two to three times per day. When the administration is carried out as described above, alpha$_1$ agonist activity is produced.

The route of administration of the pharmaceutical compositions of this invention and in accordance with the methods of this invention is internal, either parenteral or preferably oral, in an amount to produce the desired biological activity.

The following examples are not limiting but are illustrative of this invention.

EXAMPLE 1

A solution of 8-methoxy-2-tetralone (3.5 g., 0.2 mol.) and methoxyamine hydrochloride (25 g., 0.3 mol.) in 10 ml. of ethanol containing the minimum amount of water necessary to effect solution was titrated with 1 N sodium hydroxide to pH 8.2. The solution was concentrated, diluted with water, extracted with ether and the extracts dried over magnesium sulfate and concentrated to give 35 g. of a colorless oil. This was dissolved in 50 ml. of tetrahydrofuran, treated with 50 ml. of 1 molar borane in tetrahydrofuran and the solution refluxed for three hours. Concentrated hydrochloric acid (25 ml.) was added and the mixture refluxed for 15 minutes. The resulting precipitate was removed by filtration to give a white solid m.p. 275°. To a suspension of this in methylene chloride containing a twofold excess of acetyl chloride was added dropwise a solution of 10% sodium hydroxide till the aqueous remained basic. The mixture was stirred for an additional 30 minutes then washed with 10% sodium hydroxide, dilute hydrochloric acid and water. The organic phase was dried and evaporated to give N-(1,2,3,4-tetrahydro, 8-methoxy-2-naphthalenyl) acetamide as a white solid, m.p. 153°–154°.

To a suspension of 2.19 g. (0.01 mol.) of N-(1,2,3,4-tetrahydro-8-methoxy-2-naphthalenyl) acetamide and 2.21 g (0.01 mole) of silver trifluoromethyl acetate in 80 ml. of methylene chloride was added dropwise a solution of iodine (2.52 g.; 0.02 mole) in 80 ml. of methylene chloride. The reaction mixture was stirred for one hour at room temperature, filtered and evaporated to leave an oil to which 100 ml. of water was added. After 30 minutes the oil solidified. The crystals were collected, dried and recrystallized from ethanol to give N-(1,2,3,4-tetrahydro-5-iodo-8-methoxy-2-naphthalenyl) acetamide as a white solid m.p. 202°–3°.

To a solution of 2.25 g. (0.417 mole) of methylthio lithium in 22.5 ml. of dimethylformamide was added 2.4 g. (0.072 mole) of N-(1,2,3,4-tetrahydro-5-iodo-8-methoxy-2-naphthalenyl) acetamide and 1.35 g. (0.94 mole) of $Cu_2O$. The mixture was heated to 80° for three hours under argon. The reaction was cooled, diluted with 150 ml. of chloroform and filtered through celite. The filtrate was washed with water, dried and evaporated to give 1.8 g. of N-[1,2,3,4-tetrahydro-8-methoxy-5-(methylthio)-2-naphthalenyl]acetamide as a white solid, m.p. 190°.

A solution of 1.0 g. (3.8 mmole) of N-[1,2,3,4-tetrahydro-8-methoxy-5-(methylthio)-2-naphthalenyl]acetamide in 100 ml. of toluene containing 0.474 g. (6 mmole) of pyridine was heated to 65°. Phosphorous pentachloride (1.25 g., 6 mmol.) was added and heating continued for two hours. The toluene was removed under reduced pressure, 200 ml. of methanol was added and the solution stirred overnight at room temperature. The methanol was evaporated and 100 ml. of 1:1 tetrahydrofuran-$H_2O$ was added. After 30 minutes the tetrahydrofuran was removed and the aqueous layer was washed with ether. It was made alkaline with ammonium hydroxide and extracted with three portions of methylene chloride. The combined extracts were dried and evaporated to yield as an oil the free base, 1,2,3,4-tetrahydro-8-methoxy-5-(methylthio)-2-naphthalenamine. This was dissolved in ether and treated with excess ethereal hydrogen chloride. The resulting precipitate was removed by filtration and recrystallized from methanol-ethyl acetate-ether to give 0.45 g. of 1,2,3,4-tetrahydro-8-methoxy-5-(methylthio)-2-naphthalenamine hydrochloride as a white solid, m.p. 290° (dec.).

EXAMPLE 2

A solution of 1.1 g. (5 mmole) of 1,2,3,4-tetrahydro-8-methoxy-5-(methylthio)-2-naphthalenamine in 1.5 ml. of 98% formic acid and 1.7 ml. of 37% formaldehyde was heated at 100° for 6 hours and stirred overnight at room temperature. The mixture was acidified with 10 ml. of 3 N hydrochloric acid, washed with ether and made alkaline with ammonium hydroxide. It was extracted with methylene chloride, dried with magnesium sulfate and concentrated to an oil. This was dissolved in ether and treated with ethereal hydrogen chloride. The product was collected and chromatographed on silica gel eluting with 95:5 methylene chloride-methanol to give 1,2,3,4-tetrahydro-8-methoxy-N,N-dimethyl-5-(methylthio)-2-naphthalenamine hydrochloride as a white solid, m.p. 215°–217°.

EXAMPLE 3

A solution of N-(1,2,3,4-tetrahydro-8-methoxy-2-naphthalenyl) acetamide (2.0 g., 0.009 mole) and 20 ml. of boron trifluoride etherate in 150 ml. of methylene chloride was cooled with dry ice/acetone under argon. Trifluoromethyl sulfenyl chloride (8.0 g.; 0.058 mole) was condensed into a flask with dry ice/acetone ice bath and then bubbled into the methylene chloride in a stream of argon. The reaction mixture was stirred overnight in a pressure bottle at room temperature. The methylene chloride and excess sulfenylchloride were removed under reduced pressure and the residue dissolved in methylene chloride, washed with 5% sodium bicarbonate until basic, dried over magnesium sulfate and evaporated to give 1.75 g. (60%) of N-[1,2,3,4-tetrahydro-8-methoxy-5-(trifluoromethylthio)-2-naphthalenyl]acetamide a white solid, m.p. 201°.

To a solution of this acetamide (1.0 g.; 0.003 mole) in 25 ml. of dry tetrahydrofuran was added 10 ml. of a 1 molar solution of borane in tetrahydrofuran. The reaction mixture was refluxed for two hours, cooled, 20 ml. of 3 N hydrochloric acid added and refluxed for 20 minutes. It was concentrated and diluted with ice water (50 ml.). The resulting crystals were removed by filtration and dried to give 0.75 g. of 1,2,3,4-tetrahydro-8-methoxy-N-ethyl-5-(trifluoromethylthio)-2-naphthalenamine as a white solid, m.p. 260°.

EXAMPLE 4

In the procedure of Example 1, substituting ethylthio lithium for methylthio lithium yields the product 1,2,3,4-tetrahydro-8-methoxy-5-(ethylthio)-2-naphthalenamine.

EXAMPLE 5

To a solution of 2.0 g. (5.8 mmol.) of N-(1,2,3,4-tetrahydro-5-iodo-8-methoxy-2-naphthalenyl) acetamide in 20 ml. of dry tetrahydrofuran at −78° C. was added 1.45 g. (23.2 mmol) of n-butyl lithium. The solution was stirred for 30 minutes and then treated with 2.52 g. (116 mmol) of diphenyldisulfide in 5 ml. of tetrahydrofuran. It was stirred at room temperature overnight, decomposed with 25 ml. of water, concentrated and extracted with ether. The ether extracts were dried and evaporated to an oil which was chromatographed on silica gel eluting with 1:1 ether-ethyl acetate. Recrystallization from methanol-ether gave 900 mg. of N-[1,2,3,4-tetrahydro-8-methoxy-5-(phenylthio)-2-naphthalenyl]acetamide as a white solid, m.p. 145°–154°.

Following the procedure of Example 1 and substituting the above 5-phenylthio acetamide for N-[1,2,3,4-tetrahydro-8-methoxy-5-(methylthio)-2-naphthalenyl]acetamide yields 1,2,3,4-tetrahydro-8-methoxy-5-(phenylthio)-2-naphthalenamine as the final product.

EXAMPLE 6

A solution of 219 mg. (1 mmol) of N-(1,2,3,4-tetrahydro-8-methoxy-2-naphthalenyl) acetamide in 7.5 ml. of trifluoroacetic acid was treated with 140 mg. of sodium nitrate in one portion. It was stirred for one hour at room temperature, poured into excess sodium bicarbonate solution and extracted well with methylene chloride. The combined extracts were washed with water, dried and evaporated to give crystals. Recrystallization from ethyl acetate gave N-(1,2,3,4-tetrahydro-8-methoxy-5-nitro-2-naphthalenyl) acetamide as white crystals m.p. 205°–206°.

A solution of N-(1,2,3,4-tetrahydro-8-methoxy-5-nitro-2-naphthalenyl) acetamide (264 mg., 1 mmol.) in 30 ml of ethanol was hydrogenated for 30 minutes at 50 psi over 30 mg. of platinum oxide. The reaction was filtered through celite and treated with ethereal hydrogen chloride. The resulting precipitate was collected and crystallized from ethanol-ethyl acetate to give white crystals m.p. >260° dec. This was suspended in 10 ml. of tetrahydrofuran, treated with 6 ml. of 1 m. borane in tetrahydrofuran and refluxed for 7 hours. The solution was treated with 15 ml. of concentrated hydrochloric acid and refluxed for one hour. It was cooled in ice and the resulting precipitate removed and crystallized from methanol to give 1,2,3,4-tetrahydro-$N^2$-ethylamino-8-methoxy-2,5-naphthalene diamine as white crystals, m.p. 202° dec.

EXAMPLE 7

To a solution of 1.8 g. (7 mmole) of N-[1,2,3,4-tetrahydro-8-methoxy-5-(methylthio)-2-naphthalenyl]acetamide in 30 ml. of tetrahydrofuran was added dropwise 20 ml. of 1 molar solution of borane in tetrahydrofuran. The solution was refluxed for 2 hours, cooled and treated dropwise with 20 ml. of concentrated hydrochloric acid. The mixture was concentrated, diluted with 50 ml. of water, made alkaline with ammonium hydroxide and extracted with methylene chloride. The extracts were dried over magnesium sulfate and concentrated to an oil. This was dissolved in ether and treated with excess ethereal hydrogen chloride. The resulting precipitate was collected and recrystallized from methanol-ethyl acetate to give 1.15 g. of 1,2,3,4-tetrahydro-N-ethyl-8-methoxy-5-(methylthio)-2-naphthalenamine, white crystals, m.p. 222°–224°.

EXAMPLE 8

Following the procedure of Example 7 and using N-[1,2,3,4-tetrahydro-8-methoxy-5-(ethylthio)-2-naphthenyl]acetamide as the starting material gives 1,2,3,4-tetrahydro-N-ethyl-8-methoxy-5-(ethylthio)-2-naphthalenamine.

EXAMPLE 9

A solution of 2.23 g. (0.01 mol.) of 1,2,3,4-tetrahydro-8-methoxy-5-(methylthio)-2-naphthalenamine in 50 ml. of methylene chloride is acylated with 1.08 g. (0.01 mole) of ethylchloroformate. The product is reduced with 2.0 g. of lithium aluminum hydride in ether to give 1,2,3,4-tetrahydro-8-methoxy-N-methyl-5-(methylthio)-2-naphthalenamine.

EXAMPLE 10

Substituting 1,2,3,4-tetrahydro-8-methoxy-5-(ethylthio)-2-naphthalenamine for the starting material and following the procedure of Example 9 yields 1,2,3,4-tetrahydro-8-methoxy-N-methyl-5-(ethylthio)-2-naphthalenamine.

EXAMPLE 11

Following the procedures of Examples 1 through 10 and substituting 5-methoxy-2-tetralone for the 8-methoxy-2-tetralone derivative yields the following respective products: 1,2,3,4-tetrahydro-5-methoxy-8-(methylthio)-2-naphthalenamine
1,2,3,4-tetrahydro-5-methoxy-N,N-dimethyl-8-(methylthio)-2-naphthalenamine
1,2,3,4-tetrahydro-5-methoxy-N-ethyl-8-(trifluoromethylthio)-2-naphthalenamine
1,2,3,4-tetrahydro-5-methoxy-8-(ethylthio)-2-naphthalenamine
1,2,3,4-tetrahydro-5-methoxy-8-(phenylthio)-2-naphthalenamine
1,2,3,4-tetrahydro-$N^2$-ethylamino-5-methoxy-2,8-naphthalenediamine
1,2,3,4-tetrahydro-N-ethyl-5-methoxy-8-(methylthio)-2-naphthalenamine
1,2,3,4-tetrahydro-N-ethyl-5-methoxy-8-(ethylthio)-2-naphthalenamine
1,2,3,4-tetrahydro-5-methoxy-N-methyl-8-(methylthio)-2-naphthalenamine
1,2,3,4-tetrahydro-5-methoxy-N-methyl-8-(ethylthio)-2-naphthalenamine

EXAMPLE 12

| Ingredients | Mg./Capsule |
| --- | --- |
| 1,2,3,4-tetrahydro-8-methoxy-N,N-dimethyl-5-(methylthio)-2-naphthalenamine hydrocholride | 150 |
| Lactose | 150 |

The above ingredients are mixed and filled into a hard gelatin capsule.

One capsule is given three times a day.

EXAMPLE 13

| Ingredients | Mg./Tablet |
| --- | --- |
| 1,2,3,4-tetrahydro-8-methoxy-5-(methylthio)-2-naphthalenamine hydrochloride | 50 |
| Calcium Sulfate Dihydrate | 150 |
| Sucrose | 25 |
| Starch | 15 |
| Talc | 5 |
| Stearic acid | 3 |

The sucrose, calcium sulfate and 5-(methylthio)-2-naphthalenamine are thoroughly mixed and granulated with hot 10% gelatin solution. The wetted mass is passed through a No. 6 mesh screen directly onto drying trays. The granules are dried at 120° C. and passed through a No. 20 mesh screen, mixed with starch, talc and stearic acid and compressed into tablets.

Two tablets are administered three times a day.

What is claimed is:

1. A compound of the formula:

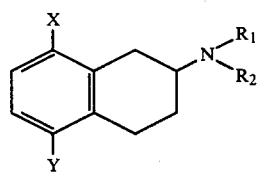

in which:

R₁ and R₂ are each hydrogen or lower alkyl having 1 to 3 carbon atoms;

X is methoxy and Y is methylthio, ethylthio, phenylthio, trifluoromethylthio or amino; or Y is methoxy and X is methylthio, ethylthio, phenylthio, trifluoromethylthio or amino;

or a pharmaceutically acceptable acid addition salt thereof.

2. The compound of claim 1 in which X is methoxy.

3. The compound of claim 2 in which Y is methylthio.

4. The compound of claim 3 in which R₁ and R₂ are hydrogen, being the compound 1,2,3,4-tetrahydro-8-methoxy-5-(methylthio)-2-naphthalenamine or a pharmaceutically acceptable acid addition salt thereof.

5. The compound of claim 4 being the compound 1,2,3,4-tetrahydro-8-methoxy-5-(methylthio)-2-naphthalenamine hydrochloride.

6. The compound of claim 3 in which R₁ and R₂ are methyl, being the compound 1,2,3,4-tetrahydro-8-methoxy N,N-dimethyl-5-(methylthio)-2-naphthalenamine or a pharmaceutically acceptable acid addition salt thereof.

7. The compound of claim 1 in which Y is methoxy.

8. The compound of claim 7 in which X is methylthio.

9. The compound of claim 8 in which R₁ and R₂ are hydrogen being the compound 1,2,3,4-tetrahydro-5-methoxy-8-(methylthio)-2-naphthalenamine or a pharmaceutically acceptable acid addition salt thereof.

10. The compound of claim 8 in which R₁ and R₂ are methyl being the compound 1,2,3,4-tetrahydro-5-methoxy N,N-dimethyl-8-(methylthio)-2-naphthalenamine or a pharmaceutically acceptable acid addition salt thereof.

11. A pharmaceutical composition in dosage unit form having alpha₁ agonist activity comprising a pharmaceutical carrier and an effective amount of a compound as defined in claim 1.

12. A pharmaceutical composition in dosage unit form having alpha₁ agonist activity comprising a pharmaceutical carrier and an effective amount of the compound as defined in claim 4.

13. A pharmaceutical composition in dosage unit form having alpha₁ agonist activity comprising a pharmaceutical carrier and an effective amount of the compound as defined in claim 5.

14. A method of producing alpha₁ agonist activity which comprises administering to an animal requiring said treatment an amount sufficient to produce said activity of a chemical compound as defined in claim 1.

15. A method of producing alpha₁ agonist activity which comprises administering to an animal requiring said treatment an amount sufficient to produce said activity of a chemical compound as defined in claim 4.

16. A method of producing alpha₁ agonist activity which comprises administering to an animal requiring said treatment a dosage unit of from about 50 mg. to about 100 mg. of a chemical compound as defined in claim 1.